United States Patent [19]

Chan et al.

[11] Patent Number: 5,198,561

[45] Date of Patent: Mar. 30, 1993

[54] RUTHENIUM-BINAP ASYMMETRIC HYDROGENATION CATALYST

[75] Inventors: Albert S. C. Chan, St. Louis; Scott A. Laneman, Creve Coeur, both of Mo.

[73] Assignee: Monsanto Company, St. Louis, Mo.

[21] Appl. No.: 665,069

[22] Filed: Mar. 6, 1991

Related U.S. Application Data

[63] Continuation-in-part of Ser. No. 620,672, Dec. 3, 1990, which is a continuation-in-part of Ser. No. 487,465, Mar. 2, 1990, which is a continuation-in-part of Ser. No. 369,875, Jun. 22, 1989, Pat. No. 4,994,607.

[51] Int. Cl.$^5$ .................................................. C07F 15/00
[52] U.S. Cl. .................................. 556/13; 556/136
[58] Field of Search .................................. 556/13, 136

[56] References Cited

U.S. PATENT DOCUMENTS

| | | | |
|---|---|---|---|
| 3,637,767 | 1/1972 | Alvarez | 260/348 |
| 3,998,966 | 12/1976 | Fried et al. | 424/308 |
| 4,008,281 | 2/1977 | Knowles et al. | 260/606.5 |
| 4,142,992 | 8/1979 | Knowles et al. | 252/431 P |
| 4,207,241 | 6/1980 | Fried et al. | 260/345 |
| 4,239,914 | 12/1980 | Campolni et al. | 562/466 |
| 4,328,356 | 5/1982 | Giordano et al. | 560/56 |
| 4,409,397 | 10/1983 | Paxson | 562/496 |
| 4,542,237 | 7/1985 | Schloemer | 562/466 |
| 4,601,797 | 7/1986 | Wagenknecht | 204/59 |
| 4,691,037 | 9/1987 | Yoshikawa et al. | 556/18 |
| 4,766,225 | 8/1988 | Sayo et al. | 556/16 |
| 4,857,462 | 8/1989 | Maier et al. | 435/197 |
| 4,962,230 | 10/1990 | Takaya | 562/433 |
| 4,962,242 | 10/1990 | Yamada | 568/822 |
| 5,012,002 | 4/1991 | Kumobayashi | 568/17 |

FOREIGN PATENT DOCUMENTS

272787A2 6/1988 European Pat. Off. .
59-51234 3/1984 Japan .

OTHER PUBLICATIONS

Qjima et al, J. Org. Chem., 45, No. 23, 4728 (1980).
Takahashi et al, Chemistry Letters, 1921 (1987).
Piccolo et al, J. Org. Chem., 52, 10 (1987).
Nayori et al, J. Am. Chem. Soc., 109, 5856 (1987).
NATO ASI Series, Series E, Applied Sciences, No. 103, Martinus Nijhoff Pub. (1986).
Asymmetric Synthesis, vol. 5, Chiral Catalysis, pp. 81–83.
J. Chem. Soc. Chem. Commun., Sep. 1989, p. 1208.

*Primary Examiner*—Paul J. Killos
*Attorney, Agent, or Firm*—Kenneth D. Goetz; Paul L. Passley; James C. Bolding

[57] ABSTRACT

A ruthenium-phosphine complex represented by the formula:

[RuXY(BINAP)]$_n$ wherein n is an integer of from 1 to about 10; and X and Y independently represent nonchelating anionic ligands.

10 Claims, No Drawings

RUTHENIUM-BINAP ASYMMETRIC HYDROGENATION CATALYST

This application is a continuation-in-part of U.S. patent application Ser. No. 07/620,672 filed Dec. 3, 1990, which is a continuation-in-part of U.S. patent application Ser. No. 07/487,465 filed Mar. 2, 1990, which is a continuation-in-part of U.S. patent application Ser. No. 07/369,875, filed Jun. 22, 1989, now U.S. Pat. No. 4,994,607.

BACKGROUND OF THE INVENTION

1. Field of the Invention

The present invention relates to a ruthenium-BINAP (Ru-BINAP) asymmetric hydrogenation catalyst and, more particularly, relates to an asymmetric hydrogenation catalyst represented by the formula:

$$[RuXY(BINAP)]_n$$

wherein n is an integer of from 1 to about 10.

2. Related Art

It is known to utilize certain Ru-BINAP complexes as catalysts for asymmetric hydrogenation reactions. For example, U.S. Pat. No. 4,691,037 discloses Ru-BINAP complexes, useful for asymmetric hydrogenations, which have the formulas:

$$Ru_2Cl_4(BINAP)_2S$$

$$RuHCl(BINAP)_2$$

wherein S represents a tertiary amine. BINAP refers to the optically active forms of BINAP and T-BINAP. These catalysts are prepared by reacting [RuCl$_2$(COD)]$_n$ (COD=cyclooctadiene), BINAP (2,2'-BIS(-DIPHENYLPHOSPHINO)-1,1'-BINAPHTHYL), T-BINAP (p-Tolyl BINAP) or p-t-Butyl-BINAP, in the presence of a tertiary amine and in a solvent such as toluene or ethanol. See also, U.S. Pat. No. 4,962,230 wherein various other Ru-BINAP complexes are disclosed as being useful in asymmetric hydrogenation reactions.

SUMMARY OF THE INVENTION

The subject invention is directed to novel Ru-BINAP asymmetric hydrogenation catalysts which are easy to prepare and more active as compared to the above-described prior art catalysts. The subject catalyst complex can be represented by the formula:

$$[RuXY(BINAP)]_n$$

wherein n is an integer of from i to about 10; and X and Y independently represent non-chelating anionic ligands, such as I, Br, Cl and F.

The subject catalysts exhibit excellent performance in asymmetric hydrogenation reactions. In particular, the subject catalysts are highly active, i.e., rate of reaction proceeds rapidly, and exhibit high selectivity, thus producing asymmetric products in high enantiomeric excess.

DETAILED DESCRIPTION OF THE INVENTION

The catalysts of the present invention can be represented by the formula $[RuXY(BINAP)]_n$ wherein n is an integer of from 1 to about 10; and X and Y independently represent nonchelating anionic ligands.

As utilized herein, the term "BINAP" refers to 2,2'-bis(diarylphosphino)-1,1'-binaphthyl compounds. Examples of such compounds include 2,2'-bis(diphenylphosphino)-1,1'-binaphthyl; 2,2'-bis(di-p-tolylphosphino)-1,1'-binaphthyl; 2,2'-bis(di-p-t-butylphenylphosphino)-1,1'binaphthyl and the like.

The term "nonchelating anionic ligands" as utilized herein refers to negatively charged ligands which do not form a chelate (i.e., having two or more atoms attached) with the Ru-BINAP complex. Examples of such ligands include halides such as I, Br, Cl and F. By contrast, noncoordinating and weakly coordinating anions are negatively charged ligands, examples of which include BF$_4$—, PF$_6$—, ClO$_4$—, BPh$_4$—and the like.

Specific examples of catalysts of the present invention include:

$$[RuCl_2(BINAP)]_n$$

$$[RuBr_2(BINAP)]"_n$$

$$[RuI_2(BINAP)]_n$$

$$[RuF_2(BINAP)]_n$$

The subject catalysts can be prepared by reacting a ruthenium-anion complex, e.g., ruthenium chloride, ruthenium bromide, ruthenium iodide, ruthenium fluoride and the like, including mixtures thereof, with cyclooca-1,5-diene (COD) in a suitable solvent to form [RuXY(COD)]$_n$, which is then reacted with a BINAP compound with heat (such as at reflux temperature of the solvent) and in a suitable solvent system. Suitable solvents for reacting the Ru-anion complex with COD include ethanol, propanol, isopropanol and the like. Suitable solvent systems for reacting RuXY(COD)$_n$ with a BINAP compound include organic acid solvents include acetic acid, propionic acid, butyric acid and the like, including mixtures thereof. Such organic acid solvents can also be combined with nonpolar organic solvents such as arene solvents, examples of which include benzene, toluene and the like, including mixtures thereof. When the solvent system is a mixture of an organic acid and a nonpolar organic solvent, such mixture can be in the range of from 1:10 to 10:1 organic aid to nonpolar solvents. Preferably, the mixture is 1:1.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Optical yields were determined by either a standard optical rotation procedure or by chiral gas chromatography of the corresponding menthol (commercially available (+)-isomer obtained from Sigma-Aldrich) ester derivatives utilizing a CHIRASIL-VAL-L column obtained from Chrompack.

EXAMPLE 1

A Fisher-Porter bottle equipped with a magnetic stirring bar was charged with 0.43 g [Ru(COD)Cl$_2$]$_n$ (from Morton Thiokol), one gram S-BINAP (from Aldrich.) and 80 mL degassed acetic acid. The mixture was stirred under N$_2$ atmosphere at about 115° C. for 18 hours. The solvent was evaporated in vacuo and the residue was powderized and used as a catalyst mixture. A $^{31}$P NMR study of this residue (FIG. 1) clearly showed that it is a mixture of Ru(BINAP) complexes which are different from previous reported Ru complexes (FIGS. 2–4). Elemental analysis of this crude mixture showed the molar ratio of Ru/BINAP/Cl to be 1/1.2/1.9.

EXAMPLE 2

Hydrogenation of Dehydronaproxen (2-6'-Methoxy-2'-Naphthyl) propenoic acid)

Five milligrams of the catalyst mixture prepared from Example 1 was dissolved in 30 g of degassed methylene chloride to make a catalyst solution. Into a 50 mL stainless steel reactor equipped with a glass liner and a magnetic stirring bar was charged with 0.2 gram of this catalyst solution, 100 mg of dehydronaproxen, 45 mg of triethylamine, and 2 g of degassed methanol (solvent). The mixture was stirred under 800 psig H$_2$ at ambient temperature for 15 hours. Analysis of the final solution by $^1$H NMR and chiral G.C. indicated 100% conversion to the hydrogenated product (naproxen) in 92% enantiomer excess (e.e.).

EXAMPLE 3

A catalyst solution was prepared by dissolving 8 mg of the Ru catalyst mixture prepared from Example 1 in 2 mL degassed dichloromethane. This catalyst solution was stirred well with 5 g 2-(p-isobutylphenyl)acrylic acid, 2.5 gm degassed triethylamine, and 100 mL degassed methanol (solvent) in a 300 mL stainless steel autoclave equipped with a magnetically driven mechanical stirrer and a temperature controlling unit under 2000 psig H$_2$ at 10° C. for 17 hours. $^1$H NMR and chiral HPLC analyses of the final product solution indicated over 99% conversion to ibuprofen in 94% enantiomer excess.

EXAMPLE 4

A catalyst solution was prepared by dissolving 5 mg of a [Ru(S-BINAP)Cl$_2$]$_n$ catalyst mixture which was prepared as in Example 1 in 3 g degassed dichloromethane. The catalyst solution was then stirred well with 0.5 g 2-methyl-2-hexenoic acid (from Bedoukian Research Inc.) in 7 g degassed methanol and one gram degassed water at 75° C. under 20 psig H$_2$ for 16 hours. Analysis of the final product indicated 100% conversion to 2-methylhexanoic acid in 80% e.e.

EXAMPLE 5

Separation of [Ru(BINAP)Cl$_2$]$_n$ Catalysts via Fractional Precipitation

One gram of mixed [Ru(S-BINAP)Cl$_2$]$_n$ catalyst prepared from Example 1 was stirred well in 50 mL degassed ethyl acetate at ambient temperature under N$_2$ atmosphere for 18 hours. The undissolved yellowish brown solid was filtered and dried under N$_2$ atmosphere to give 350 mg of product which was designated as fraction B.

The filtrate was evaporated to dryness in vacuo and the residue was shaken well with 10 mL degassed ethyl acetate and was occasionally scraped with a spatula. The undissolved solid was filtered and dried under N$_2$ atmosphere. This fraction of solid product was collected (50 mg) and designated as fraction C. The filtrate from this filtration was evaporated to dryness again in vacuo and the residue was stirred well with 10 mL degassed ethanol for 16 hours. The undissolved orange solid was filtered, washed with 10 mL degassed methanol, and dried under N$_2$ atmosphere. About 400 mg of solid was obtained and this solid was designated as fraction D. The filtrate was evaporated to dryness in vacuo and the residue was designated as fraction E.

EXAMPLE 6

Using Fractionally Precipitated [Ru(S-BINAP)Cl$_2$]$_n$ Mixed Catalysts for Asymmetric Hydrogenation A catalyst solution was prepared by dissolving 5 mg of the fraction B solid prepared from Example 5 in 30 g degassed dichloromethane. Into a 50 mL stainless steel reactor with a magnetic stirring bar was charged with 0.2 g of this catalyst solution, 100 mg of 2-(6'-methoxy-2'-naphthyl) propenoic acid, 45 mg degassed triethylamine and 2 g degassed methanol. The mixture was stirred well at ambient temperature under 800 psig H$_2$ for 15 hours. Analysis of the final product indicated 100% conversion to naproxen in 93% e.e.

EXAMPLE 7

The fraction C solid from Example 5 was used as the catalyst according to the procedure of Example 6. Analysis of the final product indicated 94% e.e. at 100% conversion.

EXAMPLE 8

The procedure of Example 6 was followed except that the catalyst used was fraction D from Example 5. Analysis of the final product indicated 100% conversion with 95% e.e.

EXAMPLE 9

A 100 mL Fischer-Porter bottle was charged with 0.103 g of [RuCl$_2$(COD)]$_n$ (0.365 mmole), 0.227 g of S-BINAP (0.0365 mmole), 5 mL of degassed acetic acid, and 5 mL of degassed toluene. The mixture was stirred well with a magnetic stirrer at 116° C. under N$_2$ atmosphere for 17 hours. Evaporation of the solution in vacuo gave 0.29 g of a red solid material. This red solid can be used as a chiral catalyst. Preferably, this red solid is further purified through recrystallization using an organic solvent such as, for example, dichloromethane, chloroform, toluene and the like.

EXAMPLE 10

This example is a comparison of catalysts prepared as in Example 9 with Ru$_2$Cl$_4$(S-BINAP)$_2$(NEt$_3$), RuCl(S-BINAP)$_2$, and Ru(OAc)$_2$(S-BINAP).

A catalyst solution was prepared by dissolving 2.6 mg of catalyst mixture from Example 9 in 13 g degassed dichloromethane. The hydrogenation reaction was carried out by magnetically stirring a mixture of 0.2 g of this catalyst solution with 100 mg 2-(6'-methoxy-2'-naphthyl)propenoic acid in 6 g degassed methanol in a 50 mL stainless steel reactor under 1000 psig H$_2$ at ambient temperature (22° C.) for 14 hours. (Triethylamine was added as a promoter in certain reactions as indicated in Table 2.) Analysis of the final product was carried out using $^1$H NMR and chiral GLC. A series of hydrogenation reactions were carried out for direct comparison of this [RuCl$_2$(S-BINAP)]$_n$ catalyst mixture with Ru(S-BINAP) prior art catalysts such as Ru$_2$Cl$_4$(S-BINAP)$_2$(NEt$_3$) and RuHCl(S-BINAP)$_2$ which were prepared according to the procedure set forth in U.S. Pat. No. 4,691,037. Ru(OAc)$_2$(S-BINAP) was prepared according to the procedure set forth in *Inorganic Chemistry*, Vol. 27, No. 3, 567 (1988 . The results of this comparison are summarized in Table 1.

TABLE 1

| Entry No. | Catalyst | Sub./Cat. (m/m) | NEt$_3$/Sub. (m/m) | Time (hr.) | Conv. (%) | ee. (%) |
| --- | --- | --- | --- | --- | --- | --- |
| 1 | [RuCl$_2$(S-BINAP)]$_n$ | 10,000 | 0 | 13.5 | 100 | 89.8 |
| 2 | [RuCl$_2$(S-BINAP)]$_n$ | 10,000 | 1 | 13.5 | 92 | 91.3 |
| 3 | [RuCl$_2$(S-BINAP)]$_n$ | 16,000 | 0 | 13.5 | 94 | 88.4 |
| 4 | [RuCl$_2$(S-BINAP)]$_2$(NEt$_3$) | 10,000 | 0 | 13.5 | 79 | 89.9 |
| 5 | [RuCl$_2$(S-BINAP)]$_2$(NEt$_3$) | 10,000 | 1 | 14.0 | 78 | 91.2 |
| 6 | [RuCl$_2$(S-BINAP)]$_2$(NEt$_3$) | 16,000 | 0 | 17.5 | 44 | 89.4 |
| 7 | HRuCl(S-BINAP)$_2$ | 16,000 | 0 | 15.0 | 30 | 90.3 |
| 8 | Ru(OAc)$_2$(S-BINAP) | 10,000 | 0 | 13.5 | 74 | 89.9 |
| 9 | Ru(OAc)$_2$(S-BINAP) | 10,000 | 1 | 14.0 | 24 | 92.4 |

Conditons are 1000 psi H$_2$ at 22° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, an make various changes and modifications of the invention to adapt it to various usages and conditions.

What is claimed is:

1. A ruthenium-phosphine complex represented by the formula:

[RuXY(BINAP)]$_n$ wherein n is an integer of from 1 to about 10; and X and Y independently represent nonchelating anionic ligands.

2. The complex of claim 1 wherein said nonchelating ligands are selected from the group consisting of halides.

3. The complex of claim 2 wherein said halides are selected from the group consisting of Br and Cl.

4. The complex of claim 2 wherein X and Y are both Cl.

5. The complex of claim 1 wherein n is 1 or 2.

6. The complex of claim 2 wherein n is 1 or 2.

7. The complex of claim 4 wherein n is 1 or 2.

8. A ruthenium-phosphine complex which is the product of a reaction between a ruthenium-nonchelating anion complex with cycloocta-1,5-diene in a suitable solvent followed by reaction of a BINAP compound in a solvent system which includes an organic acid solvent.

9. The complex of claim 8 wherein the organic acid solvent is selected from the group consisting of acetic acid, propionic acid and butyric acid.

10. The complex of claim 8 wherein the organic acid solvent is heated.

* * * * *